(12) United States Patent
Najafi

(10) Patent No.: US 11,504,003 B2
(45) Date of Patent: Nov. 22, 2022

(54) ANCHORS AND ANCHORING METHODS FOR IMPLANTABLE DEVICES

(71) Applicant: Integrated Sensing Systems, Incorporated, Ypsilanti, MI (US)

(72) Inventor: Nader Najafi, Ann Arbor, MI (US)

(73) Assignee: UIM Pressure Implant Inc., Ypsilanti, MI (US)

( * ) Notice: Subject to any disclaimer, the term of this patent is extended or adjusted under 35 U.S.C. 154(b) by 608 days.

(21) Appl. No.: 16/556,089

(22) Filed: Aug. 29, 2019

(65) Prior Publication Data

US 2021/0059527 A1 Mar. 4, 2021

(51) Int. Cl.
*A61B 5/00* (2006.01)
*A61B 17/00* (2006.01)
*A61B 5/0215* (2006.01)

(52) U.S. Cl.
CPC .......... *A61B 5/0031* (2013.01); *A61B 5/6862* (2013.01); *A61B 5/6882* (2013.01); *A61B 17/0057* (2013.01); *A61B 5/0215* (2013.01); *A61B 5/686* (2013.01); *A61B 2560/0219* (2013.01); *A61B 2560/0406* (2013.01); *A61B 2562/0233* (2013.01)

(58) Field of Classification Search
CPC ... A61B 5/0031; A61B 5/6882; A61B 5/0057; A61B 5/686
See application file for complete search history.

(56) References Cited

U.S. PATENT DOCUMENTS

| | | |
|---|---|---|
| 3,874,388 A | 4/1975 | King et al. |
| 6,309,350 B1 | 10/2001 | Van Tassel et al. |
| 6,409,674 B1 | 6/2002 | Brockway et al. |
| 8,764,848 B2 * | 7/2014 | Callaghan .......... A61B 17/0057 623/23.72 |
| 2002/0077555 A1 | 6/2002 | Schwartz |
| 2002/0077556 A1 | 6/2002 | Schwartz |
| 2004/0116992 A1 | 6/2004 | Wardle et al. |

(Continued)

FOREIGN PATENT DOCUMENTS

| | | | |
|---|---|---|---|
| CN | 111358511 A | * 7/2020 | |
| EP | 1891902 A1 | * 2/2008 | ......... A61B 17/0057 |
| WO | 2016131020 | 8/2016 | |

OTHER PUBLICATIONS

International Search Report & Written Opinion for International Application No. PCT/US2019/048936, dated May 27, 2020, (14 pages).

*Primary Examiner* — Daniel L Cerioni
*Assistant Examiner* — Raymond P Dulman
(74) *Attorney, Agent, or Firm* — Hartman Global IP Law; Gary Hartman; Domenica N. S. Hartman

(57) ABSTRACT

Anchors and anchoring methods suitable for use with implantable assemblies that include an implantable device, including but not limited to implantable sensing devices and implantable wireless sensing devices adapted to monitor physiological parameters within living bodies. Such an implantable device has a housing containing a transducer, electrical circuitry, and an antenna. The transducer is located at a first end of the housing opposite a second end of the housing. At least the transducer is located within a housing portion of the housing in which the antenna is not located. The implantable assembly further includes an anchor is adapted for securing the implantable device within a living body.

31 Claims, 6 Drawing Sheets

(56) References Cited

U.S. PATENT DOCUMENTS

| | | |
|---|---|---|
| 2004/0260346 A1 | 12/2004 | Overall et al. |
| 2006/0116590 A1* | 6/2006 | Fayram ................ A61B 5/0215 600/508 |
| 2010/0191088 A1* | 7/2010 | Anderson .............. A61B 34/20 606/300 |
| 2012/0022507 A1 | 1/2012 | Najafi et al. |
| 2013/0144379 A1 | 6/2013 | Najafi et al. |
| 2018/0116516 A1 | 5/2018 | Najafi |

* cited by examiner

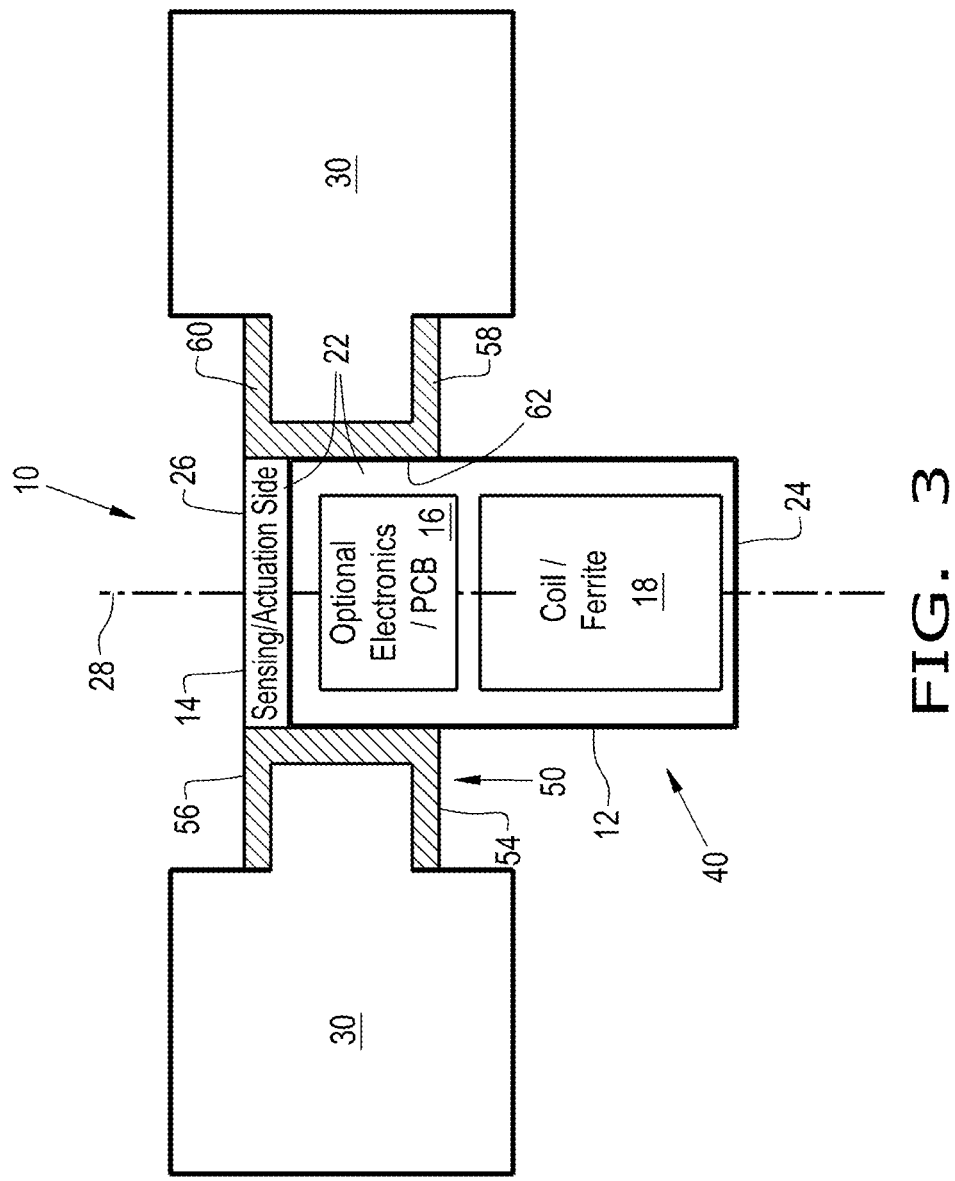

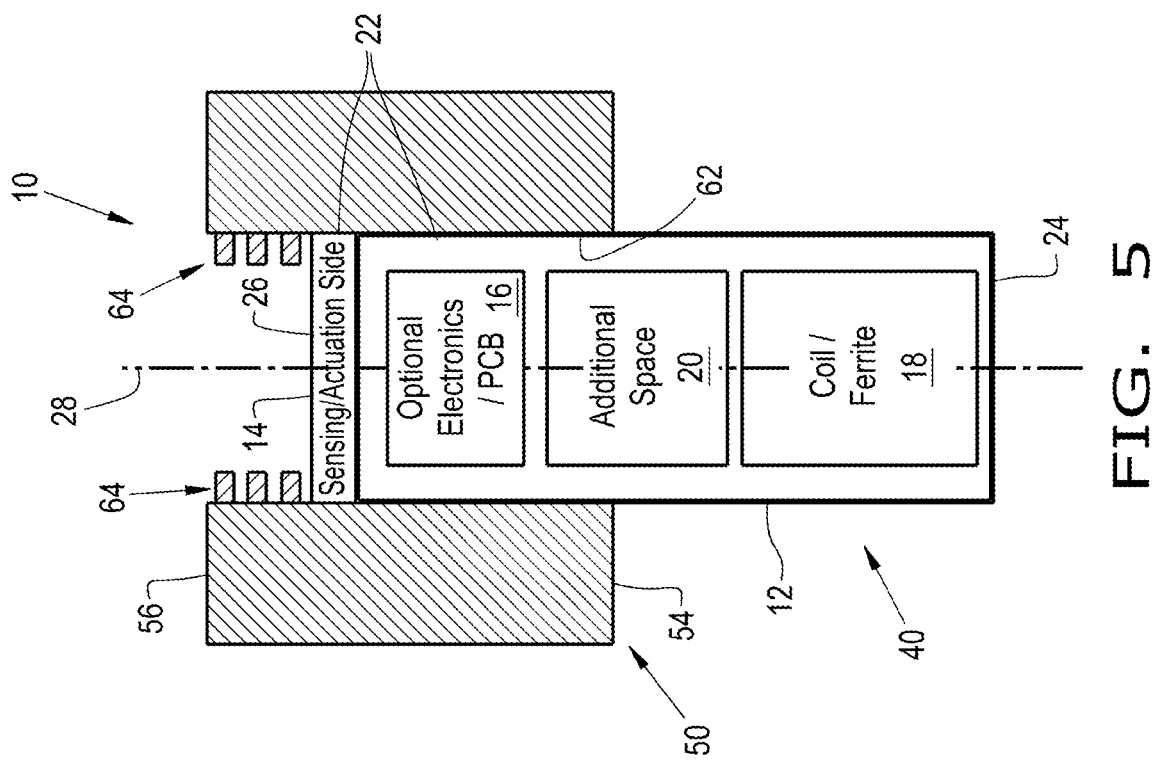
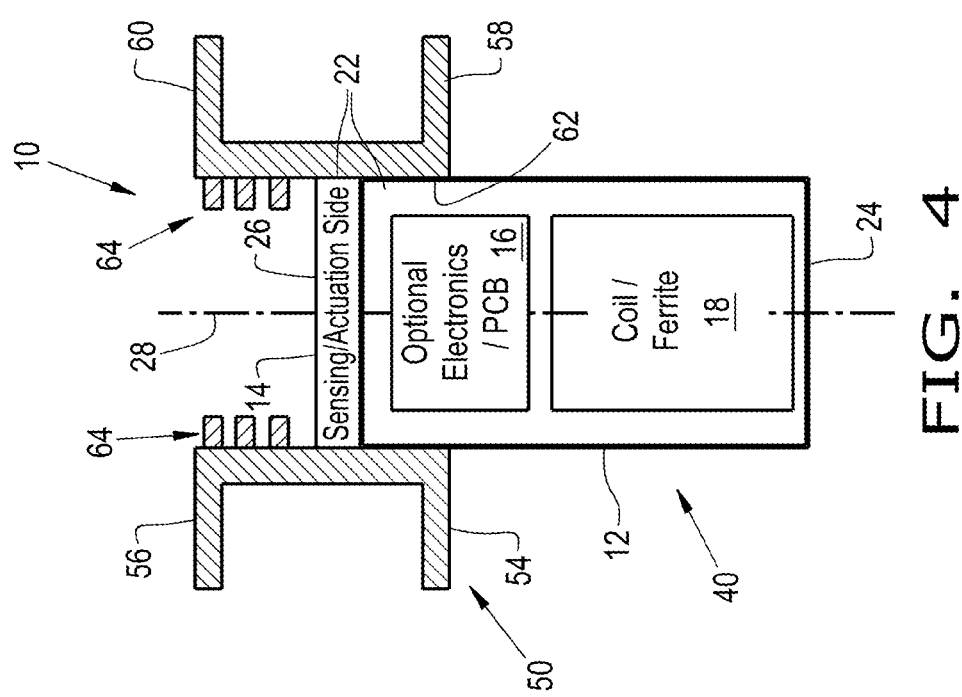

ANCHORS AND ANCHORING METHODS FOR IMPLANTABLE DEVICES

BACKGROUND OF THE INVENTION

Various patents pertain to procedures, systems, and implantable sensing devices suitable for monitoring physiological parameters within living bodies, as nonlimiting examples, U.S. Pat. Nos. 8,744,544, 8,715,300, 8,696,693, 8,512,252, 8,322,346, 8,267,863, 8,014,865, 7,860,579, 7,686,762, 7,634,319, 7,615,010, 7,317,951, and 6,968,743. Some of the inventions disclosed in these patents particularly pertain to anchoring and delivery of implantable wireless hermetically-sealed sensing devices by percutaneous methods or minimally invasive surgery (MIS), as well as by surgical procedures. While the innovations disclosed in these patents can be applied to many different body organs and systems, of particular interest has been placement in the cardiovascular system and especially within or in the vicinity of a heart chamber to monitor one or more physiological parameters within the chamber.

Some of the inventions disclosed in the above-noted patents note the ability of using metallic devices, for example vascular closure devices, atrial septum defect occluder devices (ASD and PFO occluders), and paravalvular leak closure devices, to anchor implantable wireless sensing devices. Nonlimiting examples of such devices include the CELT ACD® produced by Vasorum Ltd. (http://vasorum.ie/) or various devices produced by Occlutech International AB (http://www.occlutech.com/index.php/en/products). However, various problems can be encountered when attempting to anchor an implantable wireless sensing device using such devices, for example, metallic vascular closure devices can have a Faraday-cage effect on a wireless sensing device that can adversely affect the range and quality of tele-powering or wireless communications of the sensing device, and stresses induced in the sensing device caused by its attachment to the closure device can adversely affect the performance of the sensing device, for example, by inducing drift. Additionally, the size and diameter of the sensing device is important because it dictates at least in part the diameter of the delivery catheter required to deliver the device.

BRIEF SUMMARY OF THE INVENTION

The present invention generally relates to anchors and anchoring methods suitable for use with implantable devices, including but not limited to implantable sensing devices and implantable wireless sensing devices adapted to monitor physiological parameters within living bodies.

According to one aspect of the invention, an implantable assembly includes an implantable device comprising a housing containing a transducer, electrical circuitry, and an antenna. The transducer is located at a first end of the housing opposite a second end of the housing. At least the transducer is located within a housing portion of the housing in which the antenna is not located. The implantable assembly further includes an anchor is adapted for securing the implantable device within a living body. The anchor surrounds the housing portion but not the antenna of the implantable device so that the anchor is sufficiently remote from the antenna to not interfere with operations thereof.

According to one aspect of the invention, an implantable assembly includes an anchor having a through-hole, and first and second implantable devices disposed in the through-hole of the anchor. The first and second implantable devices comprise at least one housing and at least one antenna. Each of the first and second implantable devices comprise a transducer within the at least one housing. The transducers are located at ends of the first and second implantable devices that are exposed by the through-hole of the anchor, which surrounds the at least one housing and is adapted for securing the first and second implantable devices within a living body.

Further aspects of the invention include methods of anchoring implantable devices to sense one or more physiological parameters of a living being, and methods of anchoring implantable devices to serve as a closure or occluder device.

Other aspects and advantages of this invention will be appreciated from the following detailed description.

BRIEF DESCRIPTION OF THE DRAWINGS

FIG. 3 schematically represents the implantable assembly of FIG. 1 anchored in a wall of an internal organ.

FIGS. 4 through 6 schematically represent implantable devices assembled with anchors of types that can be used to anchor the implantable devices in accordance with further nonlimiting embodiments of the invention.

DETAILED DESCRIPTION OF THE INVENTION

Figure 2:
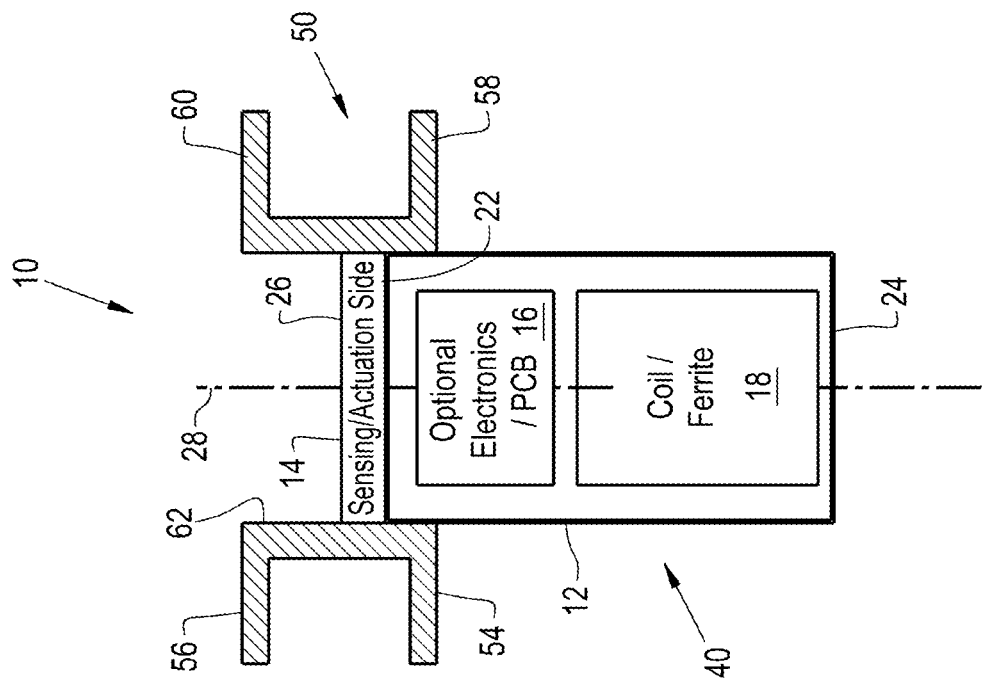
FIGS. 1 and 2 schematically represent implantable devices assembled with anchors of types that can be used to anchor the implantable devices in accordance with nonlimiting embodiments of the invention.

Illustrated in the drawings are implantable assemblies comprising implantable devices assembled with anchors adapted to anchor the implantable devices in accordance with nonlimiting embodiments of the invention. Nonlimiting examples of implantable devices include capabilities for sensing, actuation, stimulation, occlusion, and/or other mechanical function to monitor and/or manage one or more physiological parameters of a living body. The implantable devices are represented in the drawings as implantable sensing devices and particularly implantable wireless sensing devices adapted to be placed within living body, including internal organs thereof, to monitor one or more physiological parameters.

The implantable assemblies can serve as components of monitoring systems capable of monitoring a wide variety of physiological parameters, including but are not limited to those relating to the function of the circulatory, respiratory, urinary, and nervous systems. Organs of particular interest include but are not limited to the cardiovascular system, liver, brain (e.g., intracranial), kidneys, lungs, and bladder. Notable particular examples relating to the cardiovascular system include any of the four heart chambers (particularly the left ventricle and left atrium), including the left atrium appendage (LAA), and blood vessels including the inferior vena cava and blood vessels associated with the heart and lungs, for example, in a blood vessel at close proximity to the heart so that the implantable device measures physiological parameters associated with the heart (e.g., pressure, temperature, hemodynamic, O2 level, etc.). As a particular example, to monitor left atrium pressure (LA), an implantable assembly can be placed in the pulmonary vein, preferably the right superior pulmonary vein (RSPV) because in most cardiac surgeries there is an incision to place an LA succession/vent catheter as part of the normal operation. The same incision in the RSPV can be used to secure the implantable assembly. Other blood vessels can be used for different heart chambers. At the end of open chest surgery, the implantable assembly can be placed through an incision in the border between the LA and the right superior pulmonary vein used as part of routine care for placement of an LV vent. The proximal end of the implantable assembly can be sutured to the wall of the right superior pulmonary vein. Implant positioning, free from the wall of the pulmonary vein or atrium, can be confirmed with echocardiogram.

There are advantageous aspects relating to the placement of an implantable device, such as an implantable hemodynamic monitor (IHM) sensor or other type of sensor, in the inferior vena cava. The largest vein in the human body, the inferior vena cava collects blood from veins serving the tissues inferior to the heart and returns this blood to the right atrium of the heart. Although the vena cava is very large in diameter, its walls are thin due to the low pressure exerted by venous blood. The inferior vena cava forms at the superior end of the pelvic cavity when the common iliac veins unite to form a larger vein. From the pelvis, the inferior vena cava ascends through the posterior abdominal body wall just to the right of the vertebral column. Along its way through the abdomen, blood from the internal organs joins the inferior vena cava through a series of large veins, including the gonadal, renal, suprarenal and inferior phrenic veins. Blood from the tissues of the lower back, including the spinal cord and muscles of the back, enters the vena cava through the lumbar veins. Many smaller veins also provide blood to the vena cava from the tissues of the abdominal body wall. Upon reaching the heart, the inferior vena cava connects to the right atrium on its posterior side, inferior to the connection of the superior vena cava. The inferior vena cava and its tributaries drain blood from the feet, legs, thighs, pelvis and abdomen and deliver this blood to the heart. Many one-way venous valves help to move blood through the veins of the lower extremities against the pull of gravity. Blood passing through the veins is under very little pressure and so must be pumped toward the heart by the contraction of skeletal muscles in the legs and by pressure in the abdomen caused by breathing. Venous valves help to trap blood between muscle contractions or breaths and prevent it from being pulled back down toward the feet by gravity.

The drawings schematically represent the various implantable devices as comprising at least one hermetically-sealed housing that contains a transducer and electronic circuitry, for example, an application specific integrated circuit (ASIC), which operate in combination with an antenna to transmit and receive data. Preferred but nonlimiting aspects of the present invention include the ability to implant wireless sensing devices to monitor one or more physiological parameters within an organ, including the heart and blood vessels as mentioned above. The physical footprint of an implantable assembly that comprises such an implantable device is preferably limited to the implantable device, an anchor that secures the implantable device to or within the organ, and optionally a separate antenna that wirelessly transmits data and other communications to a remote device, such as a readout unit, which may also tele-power the implantable device. The physical footprint of such an implantable assembly can be far smaller than monitoring systems that must be physically connected to a relatively large remote transmitting device, for example, as in the case of the LVP-1000 Left Ventricle Pressure Monitoring System offered by Transoma Medical, Inc. Implantable wireless sensing devices utilized by the invention may employ resonant, passive, or active communication schemes described in prior patents, including but not limited to those disclosed in U.S. Pat. Nos. 8,744,544, 8,715,300, 8,696,693, 8,512,252, 8,322,346, 8,267,863, 8,014,865, 7,860,579, 7,686,762, 7,634,319, 7,615,010, 7,317,951, and 6,968,743. The wireless operation (tele-communication and/or tele-powering) of the implantable devices 40 may be accomplished by various means known in the art, such as magnetic telemetry, RF telemetry, ultrasound telemetry, analog, digital, hybrid, or mixed signal telemetry, etc.

The antenna may comprise a coil (e.g., copper windings) wrapped around an optional core (e.g., ferrite), though other antenna configurations and materials are foreseeable. The antenna may be entirely contained within the housing of the implantable device or partially or entirely located outside of the housing to allow for the diameter of the antenna to be larger from the diameter of the housing. Because the diameter of the antenna greatly affects the tele-powering and tele-communication range of the implantable device, a wider diameter antenna may eliminate the requirement for a ferrite coil, so that the implantable device requires only a coil.

The transducer, which is located at one end of the housing of the implantable device, is preferably a MEMS device, more particularly a micromachine fabricated by additive and subtractive processes performed on a substrate. The substrate can be rigid, flexible, or a combination of rigid and flexible materials. Notable examples of rigid substrate materials include glass, semiconductors, silicon, ceramics, carbides, metals, hard polymers, and TEFLON. Notable flexible substrate materials include various polymers such as parylene and silicone, or other biocompatible flexible materials. The transducer may be adapted to sense a physiological parameter of a living being. A particular but nonlimiting example of a suitable transducer for hemodynamic monitoring of various blood pressures within the cardiovascular system is a MEMS capacitive pressure sensor for sensing pressure, though other materials and any variety of sensing elements, e.g., capacitive, inductive, resistive, piezoelectric, etc., could be used. For example, the transducer could be configured to sense temperature, cardiac output, flow, acceleration, vibration, pH, conductivity, dielectric constant, chemical composition, including the composition and/or contents of a biological fluid (for example, oxygen, carbon dioxide, glucose, gene, hormone, or gas content of the fluid), and acoustics (for example, an acoustic sensor that monitors the health of the cardiovascular system or another implanted device such as ventricular assist device). Furthermore, as will be discussed below, one or more implantable devices equipped with one or more transducers can be utilized in an implantable assembly to monitor multiple physiological parameters.

The implantable device may be powered with a battery, a rechargeable battery capable of being wirelessly recharged with a remote device and/or by energy scavenging, or another power storage device, but in preferred embodiments the implantable device is wirelessly powered entirely by a remote device that is not configured for implantation, such as a readout unit. Such a readout unit may be configured to receive an output signal from the implantable device, process the signal, and relay the processed signal as data in a useful form to a user. Because the implantable device is equipped with a built-in antenna, the device requires only an anchor for implantation and does not require a wire, cable, tether, or other physical component that conducts the output of the implantable device to a separate location where another component utilizes the output of the implantable device and/or transmits the output of the implantable device to a location outside the body of the patient.

In the drawings, consistent reference numbers are used to identify functionally equivalent structures of various different implantable assemblies 10 and functionally equivalent structures of a variety of different implantable devices 40 and anchors 50 that are adapted to secure the implantable devices 40, and therefore the assemblies 10 as a whole, within a living body. As noted above, the drawings schematically represent the implantable devices 40 as comprising at least one hermetically-sealed housing 12 that contains a transducer 14 and electronic circuitry 16 which operate in combination with an antenna 18 to transmit and receive data. The implantable devices 40 may differ from each other by the placement of the antenna 18 within or outside the housing 12, as well as the arrangement of the transducer 14, circuitry 16, and antenna 18 within the housing 12. The anchors 50 may be chosen in part on the basis of the placement of the antenna 18 relative to the housing 12. The housings 12 of the implantable devices 40 may be configured to comprise a housing portion 20 (FIG. 5) that is in addition to portions of the housing 12 in which one or more internal cavities are located that contain the transducer 14 and antenna 18. As such, the additional housing portion 20 is not required to contain, and preferably does not contain, any component relating to the operation of the transducer 14 and the transmission of data to and from the implantable device 40 via the antenna 18, and therefore a cavity is not required to be present in the additional housing portion 20. The housing portion 20 is represented in FIG. 5 as located between the transducer 14 and the antenna 18, though it is also foreseeable that the housing portion 20 may form an end 24 of the housing 12 opposite the end 26 of the housing 12 where the transducer 14 is located, such that the antenna 18 is located between the transducer 14 and the housing portion 20, or may be a combination of both (i.e., the housing portion 20 may comprise two spaced-apart portions 20) that are connected together only through the housing 12 or by the anchor 50. The housing portion 20 may be integrally formed as an indiscrete region of the housing 12, or separately formed and directly attached to the housing 12, or separately formed and indirectly attached to the housing 12 with the anchor 50.

The transducer 14 and circuitry 16 will be described herein as being contained within one or more cavities of the housing 12 located at the end 26 of the implantable device 40. In addition to housing the transducer 14 and circuitry 16, a portion 22 of the housing 12 containing part of or the entireties of the transducer 14 and circuitry 16 can be dedicated to the attachment of the anchor 50 to the implantable device 40. In particular, the housing portion 22 enables the implantable device 40 to be secured with an anchor 50 that may be entirely or partly formed of a metal and/or may be used alone or in combination or integrated with another medical device (as described below), such that the antenna 18 is sufficiently remote from the anchor 50 that metallic portions of the anchor 50 do not interfere with the operation of the antenna 18. As an example, the housing portion 22 preferably creates a spacial axial distance between the antenna 18 and anchor 50 (or metallic portions thereof) to reduce Faraday-cage effects otherwise caused by metal.

The attachment of the implantable devices 40 to their anchors 50 can be accomplished in different ways, including but not limited to one or more of the following: attachment by adhesives, mechanical devices such as springs (e.g., spring wrapping or spring-force attachment), loops, fasteners, grips, or connections (e.g., fingers, loops, spirals, etc.) formed of PEEK, NiTi, etc., threads (e.g., the housing 12 is threaded into the anchor 50), welding, laser attachment, compression, thermal compression, or a combination thereof.

Figure 1:
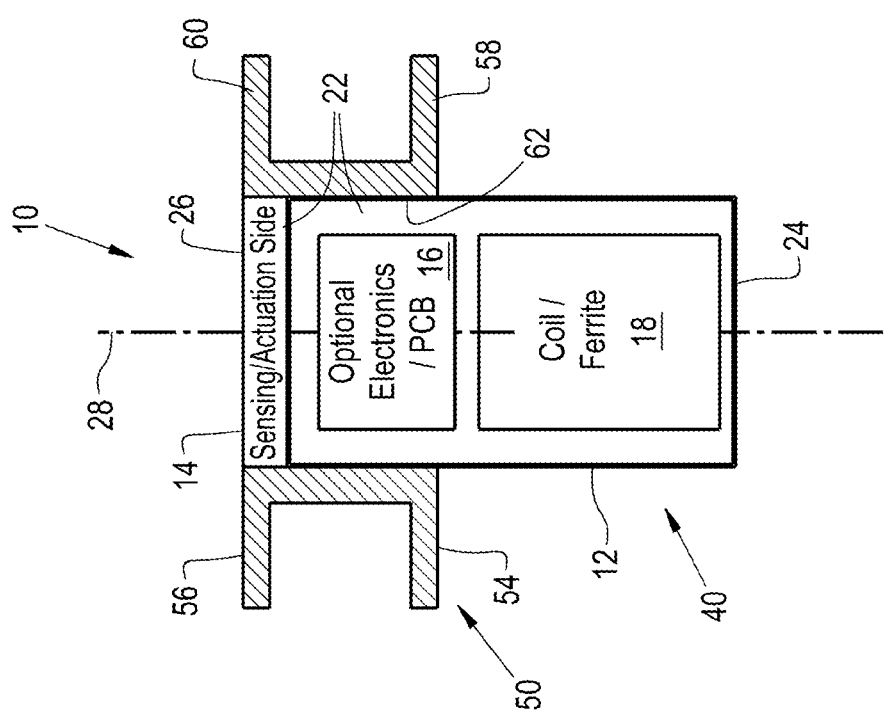

FIGS. 1 and 2 schematically represent implantable assemblies 10 whose anchors 50 have a generally cylindrical outline and define an axis that may be an axis of rotational symmetry of the anchors 50 and coincide with an axis 28 of the assemblies 10. Each of the anchors 50 has oppositely-disposed ends 54 and 56, and in some embodiments the ends 54 and 56 are defined by axial spaced rings or flanges 58 and 60, respectively. The flanges 58 and 60 can be of various sizes and formed of one or more materials, including rigid and/or flexible materials. A portion of the exterior of each anchor 50 depicted in FIGS. 1 and 2 is defined by an outer cylindrical-shaped surface, which in the case of the anchors 50 of FIGS. 1 and 2 is between the flanges 58 and 60. The anchors 50 are represented as having a through-hole 62 in which the implantable device 40 is received, though it is foreseeable that the anchors 50 could have a blind hole, or the flanges 58 and 60 could be defined by two discrete rings that are not connected to each other but define two separate through-holes 62, or comprise be defined by two discrete rings that are interconnected to each other by longitudinal legs to define the through-hole 62 within the anchor 50. The anchors 50 (and, if present, their flanges 58 and 60) may be formed or fabricated from a variety of rigid and/or flexible materials, including but not limited to metals including stainless steels and shape-memory alloys (e.g., NiTi alloys), polymers including PEEK and thermoplastic polyurethanes (TPUs), or combinations thereof.

While represented as a discrete component dedicated as an anchor, the anchors 50 disclosed herein may be part of or used in combination with another implantable device, as nonlimiting examples, a vascular closure device, a closure or occluder device (including atrial septum defect (ASD) occluders, left atrium appendage (LAA) occluders, patent foramen ovale (PFO) occluders), a stent (including but not limited to vein stents, pulmonary stents, coronary stents, and intracranial stents), a paravalvular leak closure device, an atrial flow regulator (AFR) device (also known as left atrial shunt devices), a vascular reconstruction device, a heart valve, or a heart valve repair product. Commercially available examples of such implantable medical devices include, but are not limited to, products available from Vasorum Ltd. (e.g., CELT ACD®), Occlutech International AB (e.g., PFO, AASD, UNI, PDA, Hubless PDA, PLD, mVSD, PmVSD, AFR, etc.), Boston Scientific (e.g., WATCHMAN™), Abbott (e.g., Amplatzer® ASD/PFO occluders), Cardia, Inc. (e.g., Ultrasept ASD, Ultrasept PFO, Ultrasept LAA, Ultrasept cribriform device, fenestrated fontan occluder, etc.), W. L. Gore & Associates (e.g., GORE® CARDIOFORM septal occluder, GORE® TAG® thoracic endoprosthesis, GORE® VIABAHN® VBX balloon expandable endoprosthesis, etc.), MicroPort Scientific Corporation (e.g., coronary stent systems, AAA/TAA stent graft systems, intracranial stent systems, etc.), Lepu Medical Technology (e.g., coronary stents, coronary balloons, PCI accessories, occluders, vascular plugs, heart valves, etc.), Medtronic, Biotronik SE & Co. KG, V-Wave Ltd. (V-Wave left atrial shunt devices), and Corvia Medical, Inc. (interatrial shunt device (IASD). Other anchor configurations and products are also within the scope of the invention. The anchors 50 may be coupled or attached to such additional devices as a result of being configured to include a recess, meander shape, groove, or threads, or an extension, disk, or other protruding feature, or a combination thereof.

In the embodiment of FIG. 1, the anchor 50 surrounds the portion 22 of the housing 12 that contains the entire transducer 14 and most but not all of the circuitry 16, and the end 26 of the housing 12 is flush with the flange 60 of the anchor 50. In the embodiment of FIG. 2, the anchor 50 surrounds the portion 22 of the housing 12 that contains the entire transducer 14 but none or only a minor portion of the circuitry 16, and the end 26 of the housing 12 is not flush with the flange 60 of the anchor 50 but instead is recessed within the through-hole 62. In both cases, the housing portion 22 creates a spacial axial distance between the antenna 18 and anchor 50 (or metallic portions thereof) to reduce Faraday-cage effects otherwise caused by metal. If the implantable assembly 10 is implanted so that the end 26 of the housing 12 containing the transducer 14 faces, for example, the left atrium (LA), the transducer 14 can measure LA parameters of interest, for example, LA pressure and/or temperature. The implantable assembly 10 can also be implanted in the left atrium appendage (LAA) so that the end 24 of the housing 12 faces the left atrium and the end 26 containing the transducer 14 faces LA, in which case the transducer 14 will measure the pressure within the LAA sack. Yet another example is to implant the assembly 10 in a left atrium shunt to measure parameters of the left and/or right atrium. As will be discussed below, it is also within the scope of the invention to mount two implantable devices 40 with a single anchor 50, so that two transducers 14 can simultaneously sense two different physiological parameters, for example, LA pressure and pressure within the LAA sack.

FIG. 3 represents the implantable assembly 10 of FIG. 1 anchored by the anchor 50 in a wall 30 of an organ such that the anchor 50 secures the implantable device 40 to the organ wall 30. In particular, the wall 30 of the organ is shown as being gripped between the axially-spaced flanges 58 and 60 of the anchor 50. The wall 30 may be, as nonlimiting examples, the wall of a heart ventricle or atrium, the atrial or ventricle septum, the wall of a blood vessel, etc. As evident from FIG. 3, the implantable device 40 sufficiently extends through the through-hole 62 of the anchor 50 so that the anchor 50 contacts and surrounds or circumscribes only that part of the housing 12 that is formed by the housing portion 22, such that the anchor 50 is radially aligned with the housing portion 22 with respect to the axis 28 of the implantable assembly 10 and spaced an axial distance from the antenna 18 so as not to have a negative effect or to have a minimal negative effect on the function of the internal antenna 18. The end 26 of the implantable device 40 containing the transducer 14 is not flush with the flange 60 of the anchor 50, but instead is recessed within the through-hole 62, consistent with the embodiment of FIG. 1.

FIGS. 4 and 5 represent implantable assemblies 10 configured so that, similar to the embodiment of FIGS. 1 and 3, the end 26 of the implantable device 40 containing the transducer 14 is not flush with the flange 60 of the anchor 50, but instead is recessed within the through-hole 62. The through-hole 62 of each anchor 50 of FIGS. 4 and 5 is equipped with internal threads 64 as means for attaching the implantable assemblies 10 to a delivery system, such as a catheter, nonlimiting examples of which include known delivery catheters equipped with screws to deliver ASD, PFO, and LAA occluders and AFR devices. As depicted in FIGS. 4 and 5, the housing portion 22 may occupy roughly one-half of the axial length of the through-hole 62, with the threads 64 occupying the remaining half. A spring-force device may be utilized to bias the implantable device 40 toward and possibly against the threads 64. Alternatively or in addition, the exterior of the anchors 50 could be equipped with one or more external features, as nonlimiting examples, external threads or extensions or protuberances of various shapes and sizes, as means for attaching the implantable assemblies 10 to a delivery system. The anchor 50 of FIG. 4 is structurally similar to the anchor 50 depicted in FIGS. 1 through 3 with the addition of the threads 64, whereas the anchor 50 of FIG. 5 is represented as a solid tube without discrete flanges, such that the anchor 50 has an outer cylindrical-shaped surface that extends along the entire longitudinal length of the anchor 50. In both cases, the anchor 50 is radially aligned with the housing portion 22 with respect to the axis 28 of the implantable assembly 10 and spaced an axial distance from the antenna 18 so as not to have a negative effect or to have a minimal negative effect on the function of the internal antenna 18.

Figure 6:
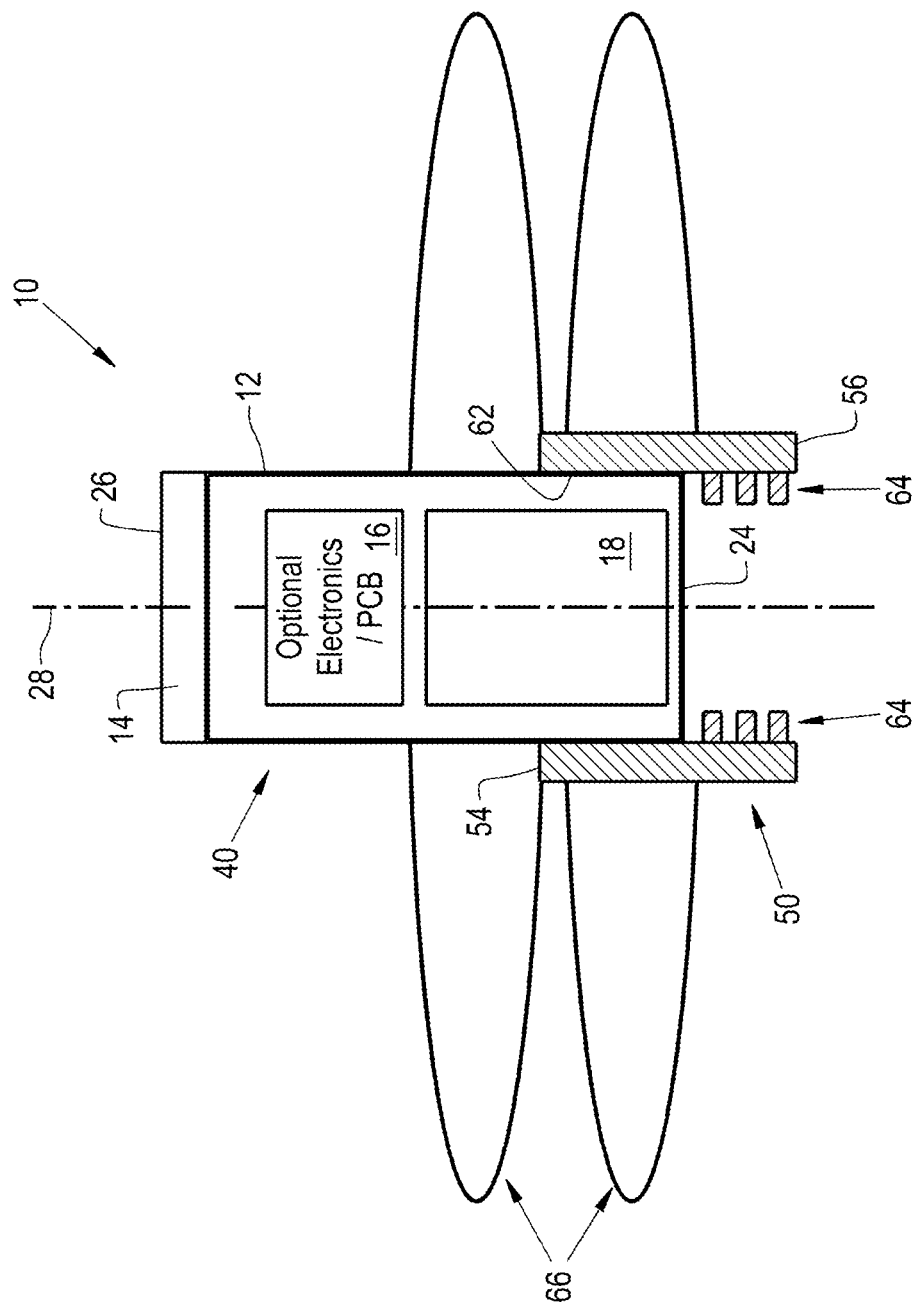

FIG. 6 represents an implantable assembly 10 comprising an implantable device 40 and an anchor similarly configured to that of FIG. 5, but further equipped with an ASD/PFO occluder 66 mounted to the anchor 50. The occluder 66 renders the assembly 10 of FIG. 6 particularly suitable for placement in the atrial septum defect (ASD) or LAA sack. In FIG. 6, the end 24 of the assembly 10 is close to the threads 64, unlike FIG. 4 and in which the ends 26 of the assemblies 10 are close to the threads 64.

Though the implantable devices 40 have been described above as having transducers 14 located at only one end of the devices 40, any one of the devices 40 may have two transducers 14 at opposite ends of the housing 12. The transducers 14 may share one or more of the internal components of the device 40. For example, the implantable device 40 may have a single antenna 18 that is shared by two transducers 14, each having separate circuitry 16. Furthermore, the antenna 18 may comprise a single ferrite core and two separate coils, one for each transducer 14 and its circuitry 16. Alternatively, the transducers 14 may have entirely separate and independent internal components within the housing 12.

Figure 8:
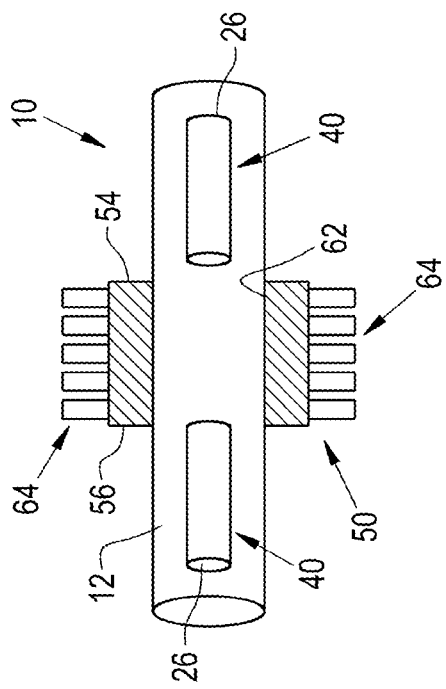
Figure 9:
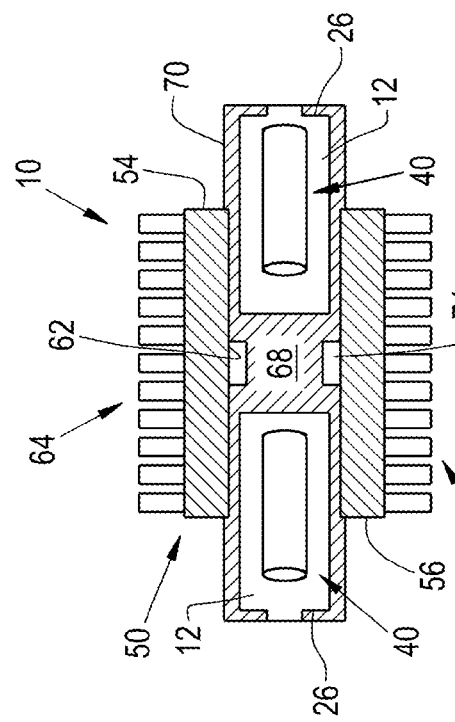
Figure 10:
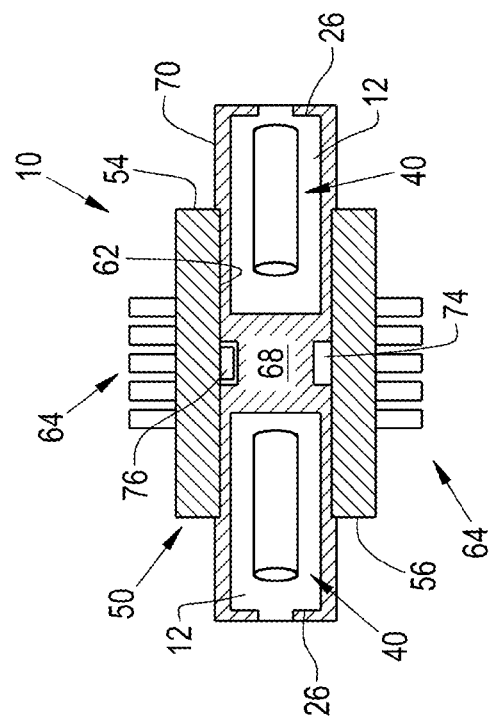

FIGS. 7 through 12 represent implantable assemblies 10 that comprise two separate implantable devices 40. In FIGS. 7 through 9, 11, and 12, each device 40 has a separate housing 12, transducer 14, circuitry 16, and antenna 18 as described previously for the embodiments of FIGS. 1 through 6. In FIG. 10, both devices 40 are enclosed in the same housing 12, and may share or have a separate transducer 14, circuitry 16, and/or antenna (coils and/or cores) 18. Signals generated by the two implantable devices 40 may be superimposed (modulated) on a carrier frequency by analog scheme(s) and then read by an external readout unit. Alternatively, the signals for the two implantable devices 40 may be superimposed on a carrier frequency by digital scheme(s) and then read by an external readout unit. Still further, a combination of analog and digital schemes could be utilized.

Figure 7:
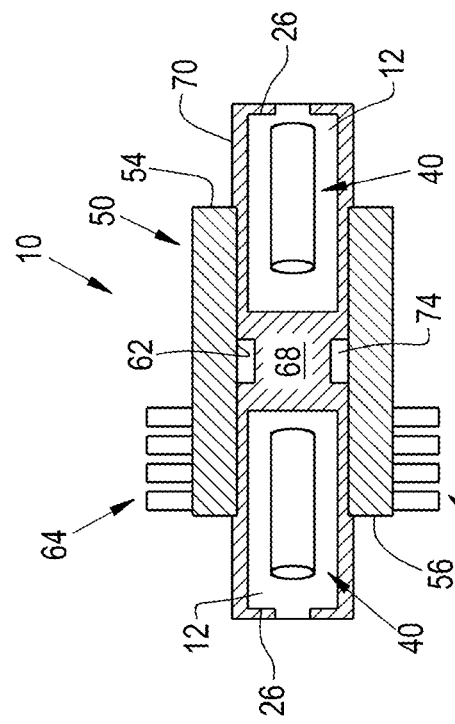
FIGS. 7 through 12 schematically represent pairs of implantable devices assembled with anchors of types that can be used to anchor the pairs of implantable devices in accordance with further nonlimiting embodiments of the invention.
Figure 12:
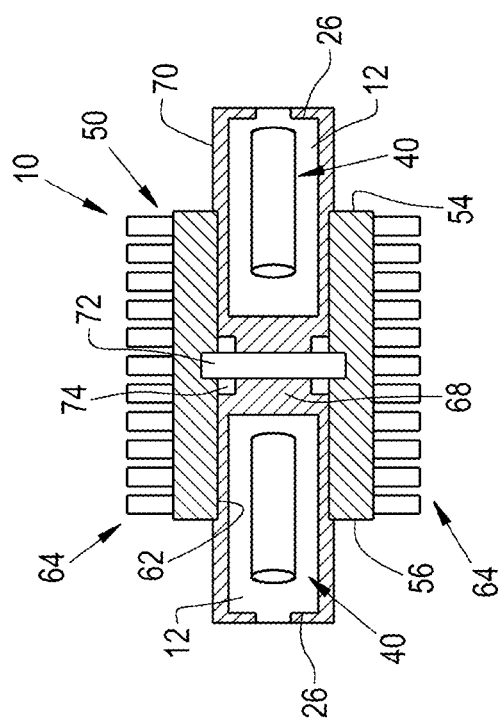
Figure 11:
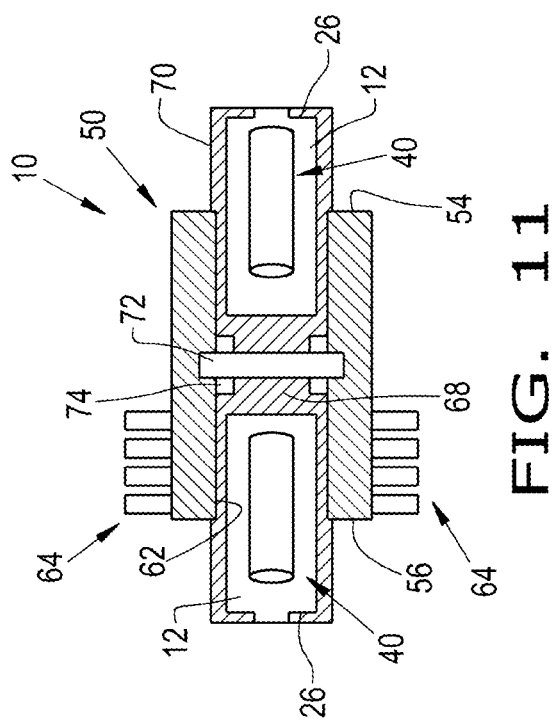

The paired implantable devices 40 are shown as axially aligned and assembled within the through-holes 62 of the anchors 50, which comprise external threads 64 on their outer cylindrical-shaped surfaces as means for attaching the implantable assemblies 10 to a delivery system. The threads 64 are distributed along the entire axial lengths of the anchors 50 shown in FIGS. 7, 10, and 12, are distributed along a limited portion of the axial lengths of the anchors 50 shown in FIGS. 8, 9, and 11, are centrally located along the axial length of the anchor 50 of FIG. 9, and are located at one axial end of each anchor 50 shown in FIGS. 8 and 11. Though only external threads 64 are shown in FIGS. 7 through 12, the anchors 50 may be equipped with internal threads if the implantable devices 40 and anchors 50 are mutually sized so that the end(s) 26 of one or both devices 40 are recessed within the through-hole 62 of their respective anchor 50. As previously described, the implantable devices 40 shown in FIGS. 7 through 12 may be secured in their anchors 50 by various means.

The implantable devices 40 of FIG. 10 are represented as sharing a single hermetically-sealed housing 12, whereas the devices 40 of FIGS. 7 through 9, 11, and 12 are each separately enclosed in a separate hermetically-sealed housing 12. Also in FIGS. 7 through 9, 11, and 12, the housings 12 are held with a wrap or sleeve 70 that surrounds adjacent ends of the housings 12. The sleeve 70 may cover a portion or the entire longitudinal length of each housing 12 and, in the embodiments shown, further may optionally cover at least a portion of the ends 26 of the housings 12 where the transducers 14 of their implantable devices 40 are located, leaving exposed at least a portion of the end 26 of each housing 12 that protrudes from the ends 54 and 56 of the anchor 50 so that the sleeve 70 does not interfere with the sensitivity or sensing capability of their associated transducer 14. Alternatively, the sleeve 70 may cover the end 26 of one or both housings 12, in which case the sleeve 70 is preferably formed of a material that reduces potential adverse effects (such as drift). The sleeve 70 may be formed of a rigid material or formed of a flexible material to facilitate flexing of the implantable devices 40 during delivery with a delivery catheter, particularly in paths with sharp angles. The sleeve 70 may be a single discrete component or fabricated from multiple components or materials. As a nonlimiting example, an outer portion/member of the sleeve 70 may be formed of a biocompatible material (such as a TPU), while an inner portion/member of the sleeve may be formed of a material that provides better mechanical support. In such an embodiment, the outer portion/member of the sleeve 70 may cover the distal end of each implantable device 40 to prevent or inhibit cell growth (for example, to avoid blood clots and/or prevent sensor drift), while other portions of the sleeve 40 are not covered by biocompatible material to provide better mechanical strength or a leak-proof connection to the anchor 50. As an alternative to the sleeve 70, it is foreseeable that the housings 12 could be coupled together by the anchor 50 alone and/or with an adhesive, tether, wire, or other connection device.

The sleeves 70 represented in FIGS. 7 through 9, 11, and 12 define an optional tether 68 between the implantable devices 40, which creates an annular-shaped recess 74 between the tether 68 and the surrounding anchor 50. The tether 68 serves as a spacer that preferably spaces apart the antennae 18 of the implantable devices 40, such that at least a portion of each antennae (coil and/or core) 18 is not surrounded by the anchor 50. The recess 74 formed by the tether 68 can be utilized as a feature for retaining the sleeve 70 and its implantable devices 40 within the through-hole 62 of the anchor 50. As nonlimiting examples, FIG. 9 depicts a spring-force feature 76 protruding into the through-hole 62 from the interior wall of the anchor 50, and FIGS. 11 and 12 depict a pin 72 passing through the tethers 68 and recesses 74 and into the anchor 50 to secure the implantable devices 40 to their anchors 50.

The implantable assemblies 10 of FIGS. 7 through 12 can be connected to or integrated with their anchors 50 to a variety of implantable medical devices, including but not limited to those noted above and the occluder represented in FIG. 6. As a nonlimiting example, an implantable assembly 10 of FIGS. 7 through 12 combined with an ASD/PFO occluder can yield a two-sensor implantable hemodynamic monitor (IHM) that can be placed in a subject that does not need an ASD/PFO occluder device but rather requires an IHM product. A delivery system (e.g., catheter) can be temporarily connected to the implantable assembly 10 via the threads 64 on its anchor 50. In preferred embodiments, the distance between the two implantable devices 40 is longer than that portion of the anchor 50 on which the threads 64 are present.

The threads 64 may be utilized to permanently place an implantable assembly 10 in a desired location. Alternatively, other means may be employed for this purpose, including but not limited to screws, meshes, sharp fingers, barbs, tines, hooks, anchoring mechanism of the types used by ASD devices, etc.

In the embodiments described herein, the anchors 50 are secured to the housing portions 22 of the implantable devices 50 such that the antenna 18 of the implantable device 40 is sufficiently remote from the anchor 50 that any metallic portions thereof surround at least a portion of the housing portion 22 but do not surround the antenna 18 and do not interfere with its operation. The anchors 50 can be equipped with various means for securing their respective implantable assemblies 10 to a wall of an organ, as nonlimiting examples, a wall of a heart ventricle or atrium, atrial or ventricle septum, blood vessel, etc. The two transducers 14 can simultaneously sense two different physiological parameters, as nonlimiting examples, left and right atrial pressures, and left atrial pressure and pressure within an LAA sack. If the anchor 50 includes or is configured as a vascular closure device, occluder device (ASD, LAA, or PFO occluder), or paravalvular leak closure device, the assembly 10 can be used as a closure or occluder device in addition to sensing a physiological parameter of a living being.

A notable advantage of implantable assemblies 10 of the types described above include the capability of effective long-term monitoring of the cardiovascular system and organs. Data obtained with the implantable devices 40 can be used for multiple purposes, including but limited to management of cardiac diseases, such as congestive heart failure, arrhythmia, structural heart diseases, congenital heart diseases, patients with single functioning ventricle, hypotension, hypertension, etc., and long-term management of patients. Data from the implantable devices 40 may be sampled at home, at a doctor's office, in a surgery room, during post-op stay including ICU, and during hospital stay.

Implantable assemblies 10 of the types represented in FIGS. 1 through 12 can be implanted in various ways. For example, if implanted in an organ, one of the assemblies 10 may be implanted in the wall 30 of the organ so that the end 26 of the sensor housing 12 slightly protrudes into the organ, with the result that the implantable assembly 10 has little or no effect on blood flow through the organ. Alternatively, it is foreseeable that the entire implantable assembly 10 may be placed inside an organ, in which case an anchor 50 may be used to secure the implantable device 40 so that it is centrally located within the organ but is spaced apart from the walls 30 of the organ so as to have little if any effect on blood flow. For example, the anchor 50 can be equipped with one or more loops, fingers, spirals, screws, ASD-type circles, etc., that secure the implantable device 40 to oppositely-disposed walls 30 of the organ. Alternatively, the anchor 50 may be stitched to the wall 30 of the organ, such as with an anchor 50 disclosed in U.S. Pat. No. 9,168,005.

The delivery of implantable assemblies 10 of the types described above can be accomplished by percutaneous delivery, catheter delivery (preferably through the femoral vein), minimally invasive approaches, surgical approaches, or combinations thereof. The delivery procedure may be a standalone procedure or performed as part of another procedure.

While the invention has been described in terms of particular embodiments, it should be apparent that alternatives could be adopted by one skilled in the art. For example, the implantable assemblies 10, implantable devices 40, and anchors 50 could differ in appearance and construction from the embodiments described herein and shown in the drawings, functions of certain components of the implantable assemblies 10, implantable devices 40, and anchors 50 could be performed by components of different construction but capable of a similar (though not necessarily equivalent) function, and appropriate materials could be substituted for those noted. In addition, the invention encompasses additional or alternative embodiments in which one or more features or aspects of different disclosed embodiments may be combined. Accordingly, it should be understood that the invention is not necessarily limited to any embodiment described herein or illustrated in the drawings. It should also be understood that the phraseology and terminology employed above are for the purpose of describing the illustrated embodiments, and do not necessarily serve as limitations to the scope of the invention. Therefore, the scope of the invention is to be limited only by the following claims.

The invention claimed is:

1. An implantable assembly comprising:
   an implantable device comprising a housing containing at least one transducer, electrical circuitry, and an antenna, the at least one transducer being located at a first end of the housing opposite a second end of the housing, the at least one transducer being located within a housing portion of the housing in which the antenna is not located; and
   an anchor adapted for securing the implantable device within a living body, the anchor surrounding the housing portion but not surrounding the antenna of the implantable device so that the anchor is sufficiently remote from the antenna to not interfere with operations thereof;
   wherein the implantable device is a first implantable device disposed in a through-hole of the anchor, the implantable assembly further comprising a second implantable device disposed in the through-hole of the anchor, the second implantable device comprising a housing containing at least one transducer, electrical circuitry, and an antenna, the at least one transducer of the second implantable device being located at a first end of the housing of the second implantable device, the at least one transducer of the second implantable device being located within a housing portion of the housing of the second implantable device in which the antenna of the second implantable device is not located;
   wherein the housings of the first and second implantable devices are joined together by a sleeve.

2. The implantable assembly of claim 1, wherein the first end of the housing of the first implantable device at which the at least one transducer of the first implantable device is located is exposed by the through-hole.

3. The implantable assembly of claim 2, wherein the first end of the housing of the first implantable device protrudes from the through-hole of the anchor.

4. The implantable assembly of claim 2, wherein the first end of the housing of the first implantable device is recessed within the through-hole of the anchor.

5. The implantable assembly of claim 1, wherein the anchor has a metal portion that surrounds the housing portion of the first implantable device but does not surround the antenna of the first implantable device.

6. The implantable assembly of claim 1, wherein the anchor comprises means for attaching and detaching the first and second implantable devices to a delivery catheter.

7. The implantable assembly of claim 6, wherein the first implantable device is disposed in a first portion of the through-hole, and the attaching means comprises internal threads disposed in a second portion of the through-hole.

8. The implantable assembly of claim 6, wherein the anchor comprises a cylindrical-shaped outer surface, and the attaching means comprises external threads disposed on the cylindrical-shaped outer surface of the anchor.

9. The implantable assembly of claim 1, wherein the anchor is, or is connected to, or is integrated with a vascular closure device, a closure or occluder device, a stent, a paravalvular leak closure device, an atrial flow regulator device, a vascular reconstruction device, a heart valve, or a heart valve repair product.

10. The implantable assembly of claim 1, wherein the first ends of the housings of the first and second implantable devices are exposed by the through-hole of the anchor.

11. The implantable assembly of claim 1, wherein the first ends of the housings of the first and second implantable devices protrude from the through-hole of the anchor.

12. The implantable assembly of claim 1, wherein the sleeve partially or entirely covers the first and second implantable devices except for at least a portion of each of the first ends of the first and second implantable devices.

13. The implantable assembly of claim 1, wherein the sleeve comprises a spacer portion between the housings of the first and second implantable devices such that the housings do not abut end to end.

14. A method of using the implantable assembly of claim 1, the method comprising using the at least one transducer to sense at least one physiological parameter of a living being.

15. The method of claim 14, the method further comprising implanting the implantable assembly within an organ of the living body.

16. The method of claim 15, the method further comprising delivering the implantable assembly to the organ with a delivery catheter.

17. The method of claim 15, the method further comprising using the anchor to secure the implantable assembly to a wall of the organ.

18. The method of claim 17, the method further comprising gripping the wall of the organ between axially-spaced flanges of the anchor.

19. The method of claim 14, the method further comprising using the anchor as a closure or occluder device within an organ of the living body.

20. The method of claim 14, the method further comprising using the anchor as a vascular closure device, a closure or occluder device, a stent, a paravalvular leak closure device, an atrial flow regulator device, a vascular reconstruction device, a heart valve, or a heart valve repair product within an organ of the living body.

21. The method of claim 14, wherein the first and second implantable devices sense two different physiological parameters of the living body.

22. The method of claim 21, wherein the two different physiological parameters are two different cardiovascular pressures.

23. An implantable assembly comprising:
an anchor having a through-hole; and
first and second implantable devices disposed in the through-hole of the anchor, the first and second implantable devices comprising first and second housings that separately contain the first and second implantable devices and at least one antenna, each of the first and second implantable devices comprising at least one transducer within the first and second housings, the transducers being located at ends of the first and second implantable devices that are exposed by the through-hole of the anchor, the first and second housings being joined together by a sleeve;
wherein the anchor is adapted for securing the first and second implantable devices within a living body and the anchor surrounds the first and second housings.

24. The implantable assembly of claim 23, wherein at least one of the ends of the first and second implantable devices protrudes from the through-hole of the anchor.

25. The implantable assembly of claim 23, wherein at least one of the ends of the first and second implantable devices is recessed within the through-hole of the anchor.

26. The implantable assembly of claim 23, wherein the anchor comprises threads configured as means for attaching the first and second implantable devices to a delivery catheter.

27. The implantable assembly of claim 26, wherein the anchor comprises a cylindrical-shaped outer surface, and the threads are external threads disposed on the cylindrical-shaped outer surface of the anchor.

28. The implantable assembly of claim 23, wherein the anchor is, or is connected to, or is integrated with a vascular closure device, an occluder device, or a paravalvular leak closure device.

29. The implantable assembly of claim 23, wherein the anchor is, or is connected to, or is integrated with a left atrium appendage occluder device.

30. The implantable assembly of claim 23, wherein the sleeve entirely covers the first and second implantable devices except for at least a portion of each of the ends of the first and second implantable devices.

31. The implantable assembly of claim 23, wherein the sleeve comprises a spacer portion between the first and second housings such that the first and second housings do not abut end to end.

* * * * *